United States Patent [19]
Van Cott

[11] Patent Number: 5,637,476
[45] Date of Patent: Jun. 10, 1997

[54] METHOD FOR CLONING AND PRODUCING THE SFII RESTRICTION ENDONUCLEASE AND METHYLASE

[75] Inventor: Elizabeth M. Van Cott, Salem, Mass.

[73] Assignee: New England Biolabs, Inc., Beverly, Mass.

[21] Appl. No.: 50,767

[22] Filed: Apr. 21, 1993

Related U.S. Application Data

[63] Continuation of Ser. No. 465,904, Jan. 11, 1990, abandoned.

[51] Int. Cl.$^6$ .................. C12P 21/00; C12N 15/63; C12N 5/10; C07H 21/02
[52] U.S. Cl. .................. 536/23.2; 435/6; 435/172.3; 435/252.3; 435/243; 435/320.1; 336/23.2; 935/1; 935/6; 935/22; 935/33; 935/52; 935/66
[58] Field of Search .................. 536/23.2; 435/69.1, 435/293, 320.1

[56] References Cited

FOREIGN PATENT DOCUMENTS 193413  9/1986  European Pat. Off. .

OTHER PUBLICATIONS

Qiang, et al., Biotechnology Abstracts Databank, Abstract No. 84-07995 (1984).
Qiang, et al., Methods on Enzymology, 155 (part F):15-21 (1987).
Kosykh, et al., Molec. Gen. Genet. 178:717-719 (1980).
Mann, et. al., Gene 3:97-112 (1978).
Walder; et al., Proc. Natl. Acad. Sci. 78:1503-1507 (1981).
Bougueleret, et al., Nucl. Acid. Res. 12-3659-3676 (1984).
Gingeras & Brooks, Proc. Natl. Acad. Sci. USA 80:402-406 (1983).
Theriault & Roy, Gene, 19:355-359 (1982).
Blumenthal, et al., J. Bacteriology 164:501-509 (1985).
Kiss, et al., Nucl. Acid Res. 13:6403-6421 (1985).
Szomolayli, et al., Gene 10:219-225 (1980).
Janulaitis, et al., Gene 20:197-204 (1982).
Kiss & Baldauf, Gene 21:111-119 (1983).
Walder, et al., J. Biol. Chem. 258:1235-1241 (1983).
Wilson, et al. Gene 74:281-289 (1988).
Slatko, et al. Gene 74:45-50 (1988).
Lunnen, et al. Gene, 74:25-32 (1988).
Van Cott, etal. Gene, 74:55-59 (1988).
Raleigh & Wilson, Proc. Natl. Acad. Sci. USA 83:9070-9074 (1986).
Qiang & Schildkraut, Nucl. Acid. Res. 12:4507-4515 (1984).

*Primary Examiner*—Mindy B. Fleisher
*Attorney, Agent, or Firm*—David G. Conlin; Gregory D. Williams; David S. Resnick

[57] ABSTRACT

The present invention is directed to a method for cloning and producing the SfiI restriction endonuclease by 1) introducing the restriction endonuclease gene from *S. fimbriatus* into a host whereby the restriction gene is expressed; 2) fermenting the host which contains the plasmid encoding and expressing the SfiI restriction endonuclease activity; and 3) purifying the SfiI restriction endonuclease from the fermented host which contains the plasmid encoding and expressing the SfiI restriction endonuclease activity.

5 Claims, 6 Drawing Sheets

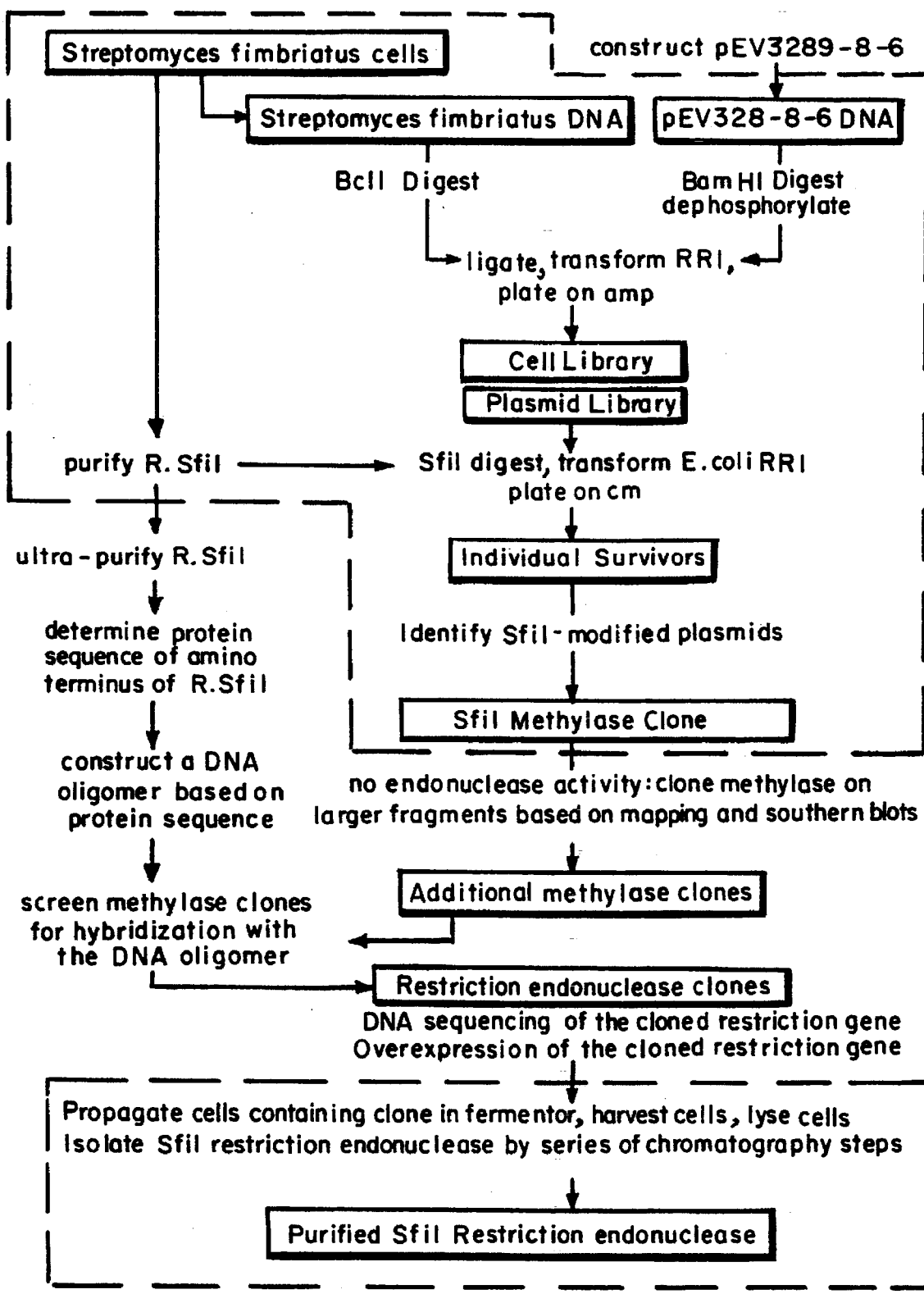
FIG. IA pEV328-8-6 is a derivative of pBR328. It has an Sfil linker (GGCCGCa/tGCGGCC) inserted at the pBR328 EcoRV site and at the first pBR328 SspI site. It is cm resistant, ap resistant, and tc sensitive.

METHOD FOR CLONING AND PRODUCING THE SFII RESTRICTION ENDONUCLEASE AND METHYLASE

This is a continuation of application Ser. No. 07/465,904 filed on Jan. 11, 1990, now abandoned.

BACKGROUND OF THE INVENTION

The present invention relates to recombinant DNA which encodes the SfiI restriction endonuclease and modification methylase, and the production of these enzymes from the recombinant DNA.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractioned into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. More than one hundred different restriction endonucleases have been identified among the many hundreds of bacterial species that have been examined to date.

Bacteria tend to possess at most only a small number restriction endonucleases per species. The endonucleases typically are named according to the bacteria from which they are derived. Thus, the species *Haemophilus aegyptius*, for example synthesizes 3 different restriction endonucleases, named HaeI, HaeII and HaeIII. Those enzymes recognize and cleave the sequences (AT)GGCC(AT), PuGCGCPy and GGCC, respectively. Escherichia coli RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by scanning the lengths of the infecting DNA molecule and cleaving them each time that the recognition sequence occurs. The breakup that takes place disables many of the infecting foreign DNA and renders that DNA susceptible to further degradation by non-specific endonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase, and it is therefore completely insensitive to the presence of the endogenous restriction endonuclease. It is only unmodified, and therefore identifiably foreign, DNA that is sensitive to restriction endonuclease recognition and attack. Together, the restriction endonuclease and modification methylase make up what is commonly referred to as the restriction-modification system ("R-M system").

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e., populations of clones derived by 'shotgun' procedures, when they occur at frequencies as low as $10^{-3}$ to $10^{-4}$. Preferably, the method should be selective, such that the unwanted, majority, of clones are destroyed while the desirable rare, clones survive.

Type II R-M systems are being cloned with increasing frequency. The first cloned systems used bacteriophage infection as a means of identifying or selecting restriction endonuclease clones (EcoRII: Kosykh et al., Molec. gen. Genet 178: 717–719, (1980); HhaII: Mann et al., Gene 3: 97–112, (1978); PstI: Walder et al., Proc. Nat. Acad. Sci. 78 1503–1507, (1981)). Since the presence of R-M systems in bacteria enable them to resist infection by bacteriophages, transformed host cells that carry cloned R-M genes can, in principle, be selectively isolated as survivors from libraries that have been exposed to phage. This method has been found, however, to have only limited value. Specifically, it has been found that cloned R-M genes do not always manifest sufficient phage resistance to confer selective survival.

Another cloning approach involves transferring systems initially characterized as plasmid-borne into *E. coli* cloning plasmids (EcoRV: Bougueleret et al., Nucl. Acid. res. 12: 3659–3676, (1984); PaeR7: Gingeras and Brooks, Proc. Natl. Acad. Sci. USA 80: 402–406, (1983); Theriault and Roy, Gene 19: 355–359 (1982); PvuII: Blumenthal et al., J. Bacteriol. 164: 501–509, (1985)).

A third approach, and one that is being used to clone a growing number of systems involves cloning by selection for an active methylase gene (See, e.g. EPO No. 193,413 published Sep. 3, 1986 and BsuRI: Kiss et al., Nucl. Acid. Res. 13: 6403–6421, (1985)). Briefly, methylase selection comprises screening for methylase clones by exposing DNA from transformed hosts with the corresponding restriction endonuclease. Survival indicates the presence of the methylase gene, presumably because the DNA of the host is modified and insensitive to attack by the restriction endonuclease. Since restriction and modification genes are often closely linked, both genes can often be cloned simultaneously. Methylase selection, however, does not always yield a complete restriction system however, but instead yields only the methylase gene (See, e.g., BspRI: Szomolanyli et al., Gene 10: 219–225, (1980); Bcn I: Janulaitis et al, Gene 20: 197–204 (1982); Bsu RI: Kiss and Baldauf, Gene 21: 111–119, (1983); and Msp I: Walder et al., J. Biol. Chem. 258: 1235–1241, (1983)), See also Wilson, Gene 74: 281–289, (1988); Slatko, et al., Gene 74: 45–50, (1988); Lunnen, et al., Gene 74: 25–32, (1988); VanCott, et al., Gene 74: 55–59, (1988).

There are, a number of possible explanations for such failures, and a variety of potential obstacles which the genetic engineer faces even in the methylase selection approach. In some systems, the cloning problem may lie in trying to introduce the endonuclease gene into a host not already protected by modification. If the methylase gene and endonuclease genes are introduced on a common DNA fragment, the methylase gene must modify or protect the host before the endonuclease gene cleaves the host's genome.

Another obstacle to cloning these systems in *E. coli* was discovered in the process of cloning diverse methylases. For example, many *E. coli* strains (including those normally used in cloning) have systems that resist the introduction of DNA containing methylation. (See, Raleigh and Wilson, Proc. Natl. Acad. Sci., USA 83: 9070–9074, (1986)). Therefore, it is also necessary to carefully consider which *E. coli* strain(s) to use for cloning.

Because highly purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

In accordance with the present invention, there is provided recombinant DNA which encodes the SfiI restriction endonuclease and modification methylase obtainable from *Streptomyces fimbriatus* (ATCC 15051) and related methods for cloning said recombinant DNA. The present invention also relates to vectors and transformed host cells which contain said recombinant DNA, to recombinant SfiI restriction endonuclease and recombinant SfiI modification methylase produced from said SfiI recombinant DNA, and to methods for producing said enzymes.

SfiI restriction endonuclease is an enzyme which recognizes the DNA sequence 5'-GGCCNNNNNGGCC-3' and cleaves between the $N_4$ and $N_5$ nucleotides, leaving a three-base 3' overhang. See, Qiang, B.-Q. and Schildkraut, I. (1984) Nucleic Acids Res. 12, 4507–4515, the disclosure of which is hereby incorporated by reference.

The preferred method for cloning the SfiI R-M system comprises constructing an appropriate vector for library construction, forming numerous libraries containing the DNA from *S. fimbriatus*, isolating clones which contain DNA coding for the SfiI modification methylase, isolating the chromosomal DNA adjacent to the SfiI modification methylase gene, and screening all the DNA containing the methylase gene for DNA coding for the SfiI restriction endonuclease. Selection for the SfiI restriction endonuclease is preferably performed by screening for clones containing DNA encoding the amino terminus of the endonuclease, which is preferably accomplished by purifying the SfiI endonuclease from *S. fimbriatus*, sequencing the the amino acid residues of the amino terminus, constructing a DNA oligomer corresponding to the amino acid sequence obtained, and screening for clones which hybridize to the DNA oligomer.

SfiI methylase and restriction endonuclease produced in accordance with the present invention is substantially pure and free of the contaminants normally found in restriction endonuclease preparations made by conventional techniques, such as that disclosed by Qiang and Schildkraut, supra.

BRIEF DESCRIPTION OF DRAWINGS

FIGS. 1A and 1B depict the scheme for cloning and producing the SfiI restriction endonuclease.

FIG. 1A illustrates the procedure employed for determining the preferred method for cloning and producing the SfiI restriction endonuclease.

FIG. 1B illustrates the preferred method for cloning and producing the SfiI restriction endonuclease based on actual results presented in FIG. 1A. At the onset of the cloning project, it was not known which endonucleases or conditions would be successful in cloning the SfiI R-M system, nor where the restriction and modification genes were located within such clones. The cloning results and subsequent DNA sequencing, mapping, and characterization of the clones described in FIG. 1A and Example 1 reveal the previously unknown direct pathway for cloning and expressing the SfiI R-M system.

DETAILED DESCRIPTION OF THE INVENTION

Figure 1B:
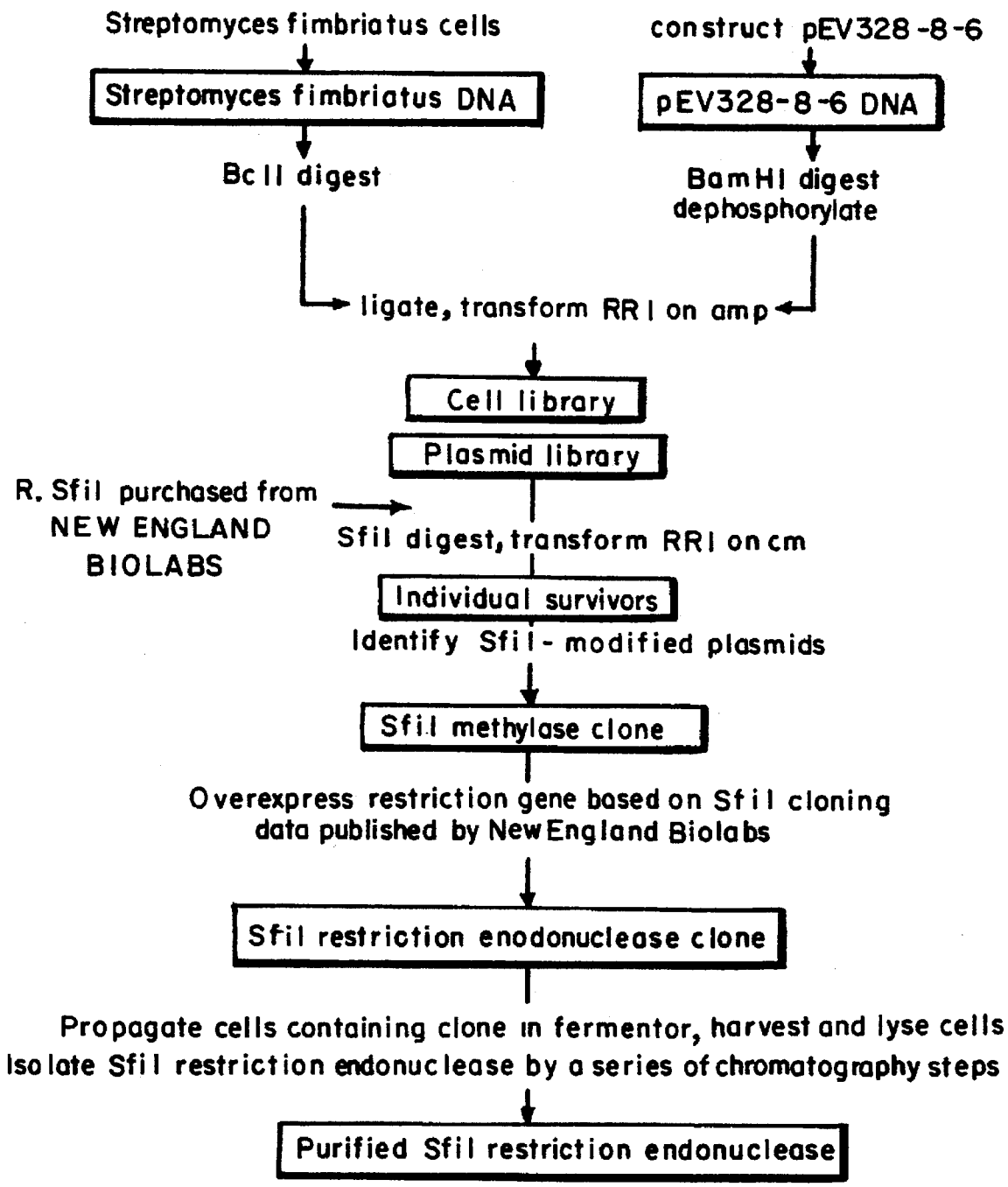

The present invention provides the first successful cloning of an R-M system recognizing an 8-base nucleotide sequence. Previously cloned systems are 4 or 6 base systems. SfiI restriction endonuclease is a particularly useful enzyme, because the SfiI recognition sequence occurs relatively infrequently in genomes, especially in AT-rich genomes such as human chromosomes. Specifically, SfiI sites are believed to occur only about once every 200,000 base pairs in human DNA. As a result, recombinant SfiI restriction endonuclease produced in accordance with the present invention will have particular utility in mapping the human genome.

The cloning of the SfiI R-M genes from *S. fimbriatus* into *E. coli* proved to be unusually difficult for a number of reasons. Unlike other previously cloned R-M systems, it has been found that SfiI endonuclease and methylase genes do not express well in *E. coli*. It is believed that the promoter endogenous to the SfiI methylase gene is not recognized by *E. coli* transcription factors. In addition, *E. coli* translation factors may not interact well with the SfiI R-M system.

Moreover, a number of modifications and variations of the methylase selection procedure described in the above-referenced EPO Publication No. 193,413 were required for the successful cloning of the SfiI R-M system. As discussed below, it was determined that methylase selection failed to produce methylase clones except when the methylase gene was cloned on a small enough DNA fragment such that the initiation codon of the methylase gene was close enough to and aligned with a promoter on the cloning vector. In such cases, the methylase gene is expressed and the clone is able to survive methylase selection, i.e, the identification of methylase clones by their ability to resist and survive SfiI digestion. In order to sucessfully clone the SfiI R-M system, a total of sixteen different restriction endonucleases were used to construct 54 libraries. Endonucleases recognizing AT-rich sequences such as HindIII, EcoRI, XbaI and NsiI were found to cleave SfiI chromosomal DNA inefficiently. After successful cloning with BclI, the Southern blot data described in Example I showed that endonucleases recognizing AT rich sequences produced fragments to large for efficient cloning.

Transformation of hosts cells at a number of different temperatures was also required as early attempts at methylase selection in cloning the SfiI R-M system were unsuccesful. For example, growth at 30° C. was used for some of the pUC19-based libraries, because pUC19 derivatives tend to be unstable at higher temperatures. The optimum temperature for growth of one preferred host, E.coli, is 37° C. However, since early attempts were unsuccessful, growth of E.coli at 42° C. was tried. It was thought that since the optimum temperature for SfiI restriction endonuclease is 50° C., it might be similarly so for the methylase. Although, the first methylase clone was obtained at 42° C., after successful cloning of the SfiI R-M system, it was determined that the optimum temperature for in vivo methylase activity in E.coli is 37° C., while the in vitro optimum temperature is 40° C.

Five different vectors were constructed in attempts to clone the SfiI R-M system. Specifically, two pBR322 derivatives, two pUC19 derivatives, and one pBR328 derivative were constructed. The pBR328 vector (described in more detail below) yielded the only active SfiI methylase clone. It is believed that cloning with pBR328 was successful because it has a higher copy number than the stable plasmid pBR322 and greater stability than very high copy number plasmid pUC19, especially at higher temperatures, i.e. greater than about 36° C. Using high-copy number plasmids increases the number of copies of the targeted recombinant DNA and thus increases methylation of the DNA. However, as noted above, the higher the copy number, the greater the instability of vectors such as pUC19, especially at high temperatures. For the SfiI R-M system, pBR328, with certain modifications, proved to have the right balance. Specifically, as discussed below, modification of pBR328 comprised insertion of SfiI sites at locations designed to maximize efficiency of methylase selection by separating that plasmid's antibiotic resistance genes from the plasmid origin of replication.

In order to improve the methylase selection step for cloning the SfiI R-M system, all plasmids of a size equal to or smaller than the cloning vector were removed from the last group of prepared libraries. Elimination of plasmids lacking an inserted DNA fragment reduced the overall number of non-methylase clone survivors, thereby improving the chance of finding the methylase clone.

Several different post-methylase selection treatments were also performed to enhance destruction of non-methylase clones. Calf-intestinal phosphatase and bacterial alkaline phosphatase were used to remove the 5' phosphate from SfiI-cleaved DNA. Exonuclease III and Bal-31 nuclease were used to remove entire nucleotides from SfiI-cleaved DNA. These treatments render SfiI-cleaved (non-methylase) plasmids less likely to religate and survive.

Two host cell strains (E.coli RRI and K802) were used in the event that transformation by a SfiI-methylase containing plasmid was lethal to one or the other. RR1 proved to be the preferred host cell for cloning the SfiI R-M system.

The above-described variations to the referenced EPO Publication 193,413 were used in a variety of combinations to construct and screen a total of 54 libraries from sixteen different library forming restriction endonucleases. As discussed below, only one of these libraries, the BclI library in pEV328-8-6, yielded a methylase clone.

After the methylase gene and DNA on both sides of the gene had been cloned and analyzed, it became possible to postulate the reasons why the majority of libraries constructed had failed to yield an SfiI R-M clone. While not wishing to be bound by theory, it is believed that the library forming endonucleases such as BglII, KpnI, PstI, SacI, SalI, SphI, and XhoI cut too far upstream of the methylase gene for the plasmid promoter to exert control over the methylase gene. Thus, since SfiI methylase does not express without plasmid promoter control, clones from these libraries could not survive methylase selection. Moreover, it was determined that BglII and SacI also cleaved within the methylase gene, further reducing the probability of obtaining an active methylase.

Two other cloning endonucleases (BamHI, XmaI) yielded a fragment containing the methylase gene that could be expressed by the plasmid promoter, but the fragment was too large (20 kb) to be efficiently cloned. Large fragments are generally much less likely to ligate into the cloning vector. (NOTE: See Example 1, step 16: after the SfiI methylase was cloned and characterized, the 20 kb BamH1 fragment was successfully isolated using a gel-purified enriched library).

The remaining six cloning endonucleases (HinP1, HpaI, NarI, Sau3AI, TaqI, XhoI (BstYI)) cut the Sfi chromosome into pieces too small to carry the desired methylase gene. Libraries were therefore constructed from partial digests of the chromosome, but no SfiI methylase clones were obtained. As discussed above and in more detail in Example 1, steps 17–18, it is believed that the partial digests did not yield fragments carrying the 5'-end of the SfiI methylase DNA close to one end of the fragment. As such no plasmids could survive methylase selection.

Once the SfiI R-M clone had been obtained, expression of the endonuclease was found to be even less efficient for the SfiI endonuclease gene. Methylase clones from many other R-M systems can be screened for restriction endonuclease activity with in vitro assays. Ordinarily, if the restriction gene is present, in vitro restriction endonuclease activity should be detected.

In contrast, endonuclease activity was not detected by in vitro assays described in the above-referenced EPO Publication 193,413 for the SfiI methylase clones. Nor did phosphocellulose column concentration of crude extracts improve this negative result. The lack of restriction activity initially indicated that either the restriction gene was not linked to the methylase gene, or it was linked but not cloned intact with the methylase gene, or it was cloned intact but not expressed.

In order to determine which of the above three possibilities was the true situation, the cloned SfiI fragment was restriction-mapped and subjected to deletion analysis to determine where the methylase gene lay within the cloned fragment. The information thus obtained was then used to determine whether there was enough DNA on either side of the methylase gene to encode an intact endonuclease restriction gene, if the two genes were linked.

In the BclI clone, it was found that there was possibly sufficient room on the right side (approximately 2 kb), but the 0.6 kb on the left side was judged not enough room to encode a gene. Thus, attempts to clone more DNA were undertaken, exploring the possibility that the lack of restriction endonuclease activity was due to the restriction gene being not present in its entirety. Specifically, a portion of the methylase gene was used to probe digests of the SfiI chromosome to generate a genomic map of the region extending beyond the boundaries of the cloned methylase DNA. This data identified certain endonucleases that cleave the R-M region into individual fragments that carry the methylase gene as well as larger amounts of adjacent DNA. The exact sizes of the fragments generated by such endonucleases were also obtained from this data. It was presumed that if the restriction and modification genes were linked, such fragments would also encode the restriction gene. The fragments were then cloned, until at least 3–4 kb DNA on each side of the methylase gene had been cloned. It was found that fragments carrying the methylase gene with the 5' end of the methylase gene close to one end of the fragment and additional DNA downstream from the 3' end of the methylase gene could express the methylase when ligated into a cloning vector in line with a vector promoter. Such fragments could therefore be isolated by methylase selection. It was also found that fragments carrying the methylase gene with additional DNA upstream from the 5' end of the methylase gene could not express the methylase when ligated into a cloning vector. It is believed that these fragments could not express the methylase because the vector promoter was too far from the methylase gene to promote expression, and indeed, the fragments could not be isolated by methylase selection. Instead, these were isolated by Grunstein blots, a procedure which identified individual plasmids that had DNA sequences identical to DNA sequences in the BclI clone.

Once at least 3–4 kb on each side of the methylase gene had been cloned among four different methylase-gene containing clones, it was presumed that if the methylase and restriction gene were linked, then the restriction gene was present in at least one of the four different methylase clones. The clones were each assayed for SfiI restriction endonuclease activity. Since no activity was detected, it was presumed that either the restriction gene was not linked to the SfiI methylase gene, or it was linked and present among the methylase clones but not expressing.

Exploring the possibility that the restriction gene was present among the methylase clones but not expressing, further attempts were undertaken to screen the SfiI methylase clones for the presence of the SfiI restriction endonuclease genes. It was necessary to make an ultra-pure preparation of the SfiI endonuclease from the S. fimbriatus and to determine the amino acid sequence of the amino terminus of the endonuclease protein. A DNA oligomer was then synthesized which correspond to the endonuclease amino acid sequence. The methylase clones were then screened for hybridization to the DNA oligomer. In this manner, the restriction gene was found to be present in two of the four different methylase clones. Thus, even though present in the clones, the restriction gene was not expressed in E. coli.

DNA sequencing and detailed mapping data of clones containing the SfiI endonuclease gene was obtained to devise methods for increasing the level of expression of the restriction endonuclease gene.

The method described herein by which the SfiI R-M system is preferably cloned and expressed is illustrated in FIGS. 1A and 1B and includes the following steps:

1. The DNA S. fimbriatus is purified using known methods.

2. The DNA is digested completely and partially with a restriction endonuclease such as BclI which cleaves the entire SfiI methylase gene into a fragment(s) which carries the 5' end of the gene at or near one end of the fragment(s). The fragment(s) should preferably be about 1.5–13 kb.

3. Cloning vectors containing SfiI sites are constructed derived from pUC19, pBR322 and pBR328. pBR328 derivative is the preferred vector. pEV328-8-6 is the most preferred vector and its construction is described in step 3 of Example 1.

4. The digested DNAs from step 2 are ligated to the cloning vector of step 3. The resulting mixtures are used to transform an appropriate host, preferably E. coli strain RR1 or K802 cells (ATCC 31343 and ATCC 33526, respectively). RR1 is the most preferred host cell.

5. The DNA/cell mixtures are plated on antibiotic media selective for transformed cells, such as media containing ampicillin or chloramphenicol. After incubation, the transformed cell colonies are pooled to form the primary cell libraries.

6. The recombinant plasmids are purified in toto from the primary cell libraries to make primary plasmid libraries.

7. In order to reduce the number of non-recombinant plasmids, the libraries are preferably electrophoresed in an agarose gel and only those plasmids greater in size than the cloning vector itself are selected for further analysis.

8. The gel-purified plasmid libraries are then digested to completion in vitro with the SfiI restriction endonuclease, which is prepared from S. fimbriatus cells. SfiI restriction endonuclease digestion causes the selective destruction of unmodified, non-methylase-containing clones, resulting in an increase in the relative frequency of SfiI methylase-carrying clones. Exonuclease and/or phosphatase may also be added to the digestion to enhance the destruction of non-methylase clones.

9. Identification of SfiI methylase clones: The digested plasmid library DNAs are transformed back into an appropriate host such as E. coli strain RR1 or K802, and transformed colonies are again obtained by plating on antibiotic plates. The colonies are picked and their DNA is analyzed for the presence of the SfiI modification gene in the following manner: Plasmid DNA is purified and incubated in vitro with SfiI restriction endonuclease to confirm resistance to digestion by SfiI. The plasmid DNA should be completely or substantially resistant to digestion.

As noted above, using the procedure described in the above-referenced EPO publication 193,413, the total cellular DNA (chromosomal and plasmid) of the clone would also be purified and incubated with SfiI restriction endonuclease at this point in the procedure. However, the E. coli chromosome contains too few SfiI sites for cleavage to be detected on ordinary agarose gels. Instead, further proof that the SfiI methylase gene has been cloned requires deleting the insert and analyzing the remaining vector for presence of intact SfiI sites, and assaying crude cell extracts from the clones for in vitro SfiI methylase activity, as described below in Example 1, step 11.

10. After it has been confirmed that the methylase gene has been cloned, clones are assayed for SfiI restriction endonuclease activity. If no activity is detected, the methylase clone is mapped and subjected to deletion analysis to determine the location of the gene within the cloned fragment. A restriction map of the S. fimbriatus chromosome in the region of the SfiI methylase is obtained. The map identifies restriction fragments that carry the SfiI methylase as well as additional, larger pieces of DNA. Since it has been found in accordance with the present invention that the restriction and methylase genes are linked, the larger methylase-containing fragments should encode the restriction gene as well.

Figure 3:
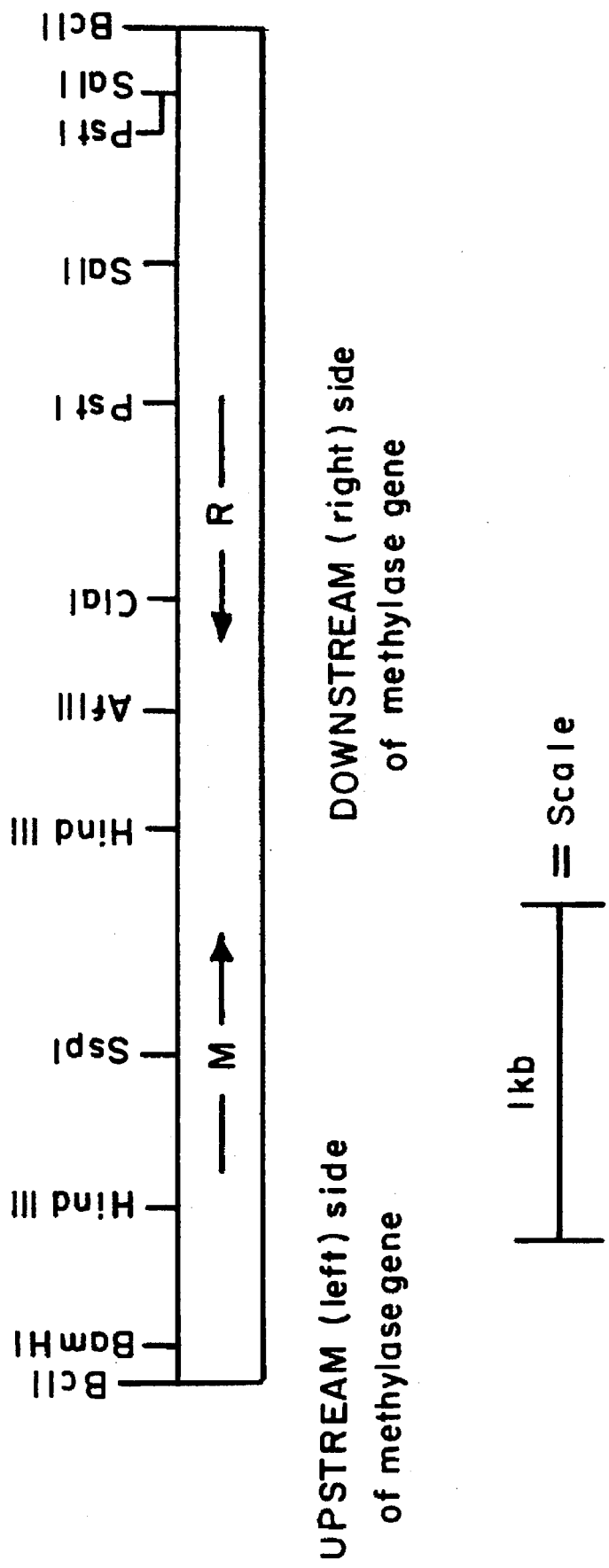
FIG. 3 is a restriction map of the original 3.9 kb BclI insert that encodes the SfiI methylase and endonuclease.

11. Libraries enriched in the methylase gene may be constructed by gel-purifying the DNA fragments described in step 10 and ligating them into an appropriate vector such as pEV328-8-6 (a derivative of pBR328, the construction of which is described in Example 1, step 3). Clones carrying DNA downstream of the methylase gene can be isolated by methylase selection; clones carrying DNA upstream or on both sides do not express but can be isolated using Grunstein blots (see FIGS. 3 and 4).

12. Identification of restriction gene clones: Clones carrying the SfiI restriction endonuclease gene were not identifiable by the crude cell extract assay described in the above-referenced EPO Publication 193,413, presumably because of the low level of expression of the SfiI endonuclease gene in *E. coli*. Therefore, the SfiI endonuclease is purified as close to homogeneity as possible from *S. fimbriatus*, and the sequence of the first 20–40 amino acids is determined. From the sequence information, a degenerate oligomer DNA probe is designed and radioactively labeled. At the same time the size of the restriction endonuclease protein is determined by protein gels to be about 32 kD, indicating that the amount of DNA necessary to encode the endonuclease gene is approximately 1 kb for SfiI. Clones carrying the SfiI restriction endonuclease are identified as those that hybridize to the restriction gene DNA probe, and carry at least 1 kb of DNA adjacent to the hybridization location. Preferably at least 1 kb of DNA is adjacent both sides of the hybridization locus. The DNA sequencing of the hybrid location will determine where the restriction endonuclease gene lies with respect to the hybridization locus.

13. Overexpression: The clone containing the restriction gene can be overexpressed using any of a number of techniques, as indicated in more detail in Example 2 below. These techniques can be used individually or in combination to obtain maximum expression of the SfiI restriction endonuclease gene.

For example, a promoter recognized strongly by *E. coli*, such as lambda pL, is inserted directly upstream of the beginning of the SfiI endonuclease gene. This transfer may be accomplished using suitable restriction endonucleases. Preferably the restriction gene should be closer to the promoter than about 0.5 kb.

A second method for increasing expression of the SfiI endonuclease gene comprises inserting a strong ribosome binding site upstream of the gene (Shine & Dalgarno 1974 *Proc. Natl. Acad. Sci. USA* 71, 1342–1346).

A third method for increasing expression of the SfiI endonuclease gene comprises altering the DNA sequence of the gene by site-directed mutagenesis or by resynthesizing the gene itself to use codons that are more efficiently utilized in *E. coli*.

Expression of the SfiI endonuclease gene can also be amplified using polymerase-chain reaction and synthetic primers hybridized to both 5' and 3' ends of the gene.

14. Production: The SfiI methylase or endonuclease may be produced from clones carrying the SfiI modification gene and the overexpressed restriction gene by propagation in a fermenter in an appropriate medium. The cells are thereafter harvested by centrifugation and disrupted by sonication to produce a crude cell extract containing SfiI methylase and restriction endonuclease activity.

15. Purification: The crude cell extract containing the SfiI methylase and endonuclease is purified by known protein purification techniques such as affinity chromatography, or ion-exchange chromatography.

Although the above-outlined steps represent the preferred mode for practicing the present invention, it will be apparent to those skilled in the art that the above described approach can vary in accordance with techniques known in the art.

The following examples are given to illustrate embodiments of the present invention as it is presently preferred to practice. It will be understood that the examples are illustrative, and that the invention is not to be considered as restricted thereto except as indicated in the appended claims.

EXAMPLE 1

Cloning of SfiI Modification Methylase and Restriction Endonuclease Genes

1. DNA purification: Lysozyme-Triton X-100 lysis followed by phenol/chloroform extractions and dialysis was found to result in a small yield of *S. fimbriatus* DNA. The Sfi cells proved to be more difficult to lyse than most other bacterial cells carrying R-M systems. Resistance to lysis seems to be a common trait among other *Streptomyces* strains and the related *Nocardia* strains, such as NaeI, NcoI, and NarI.

Addition of a freeze-thaw step during lysozyme treatment to facilitate lysis of the cells yielded a larger amount of DNA, but recovery was relatively low. Libraries, however, could be constructed using this DNA.

A more preferred method for isolation of *S. fimbriatus* DNA is described as follows: 2.5 g of cell paste was resuspended in 10 ml of 0.1M Tris-HCl, 0.1M EDTA pH 7.6. The suspension was placed in a mortar and gently mixed with a pestle which resulted in a great improvement in DNA yield. The suspension was divided into two 5.0 ml portions. 7.0 ml of 1.7 mg/ml lysozyme in 0.1M Tris-HCl, 0.1M EDTA pH 7.6 was added to each portion and each was incubated for 90 minutes at 37° C. and then overnight at 4° C. SDS was added to a final concentration of 1%, and proteinase K was added to 0.13 mg/ml and then the portions were incubated for 22 minutes at 37° C. 0.8 ml of a solution of 10% SDS and 8% sarcosyl was added to each and incubation was continued at 55° C. for 42 minutes. The two portions were then combined and dialyzed against four changes of DNA buffer (10 mM Tris-HCl, 1 mMEDTA pH 8.0) for 24 hours. The dialyzed DNA solution was then prepared for cesium chloride-ethidium bromide equilibrium density centrifugation by increasing the total volume to 80 ml with DNA buffer, and then dividing the DNA solution into four 20 ml portions, to each of which 20 grams of cesium chloride and 0.2 ml of 5 mg/ml ethidium bromide were added. The DNA solution was centrifuged at 44,000 rpm for 48 hours and the resulting band of DNA was removed by extracting 4 times with an equal volume of ice-cold water-saturated N-butanol. The cesium chloride was removed by dialysis. The DNA was then precipitated by adding NaCl to 0.5M and layering 0.55 volume isopropyl alcohol on top. The precipitated DNA was spooled onto a glass rod. The DNA was dissolved in 3 ml 10 mM Tris, 1 mM EDTA (pH 8) to a final concentration of approximately 1700 g/ml.

NOTE FOR STEPS 2–10: As noted above, a total of 16 different endonucleases were each used to digest the Sfi chromosome to construct and screen 54 libraries. Since the methylase gene did not express well enough to survive selection in all cases except the BclI library, only the details for the BclI library will be provided.

2. Complete and partial digestion: The purified DNA was cleaved with BclI endonuclease as follows: µl of DNA at 1700 µg/ml in 10 mM Tris pH 7.5, 10 mM MgCl$_2$, 50 mM NaCl, 10 mM mercaptoethanol buffer was divided into one 100 µl aliquot and five, 50 µl aliquots. To the 100 µl tube was added 10 units of BclI endonuclease (New England Biolabs, Beverly, Mass.) to achieve 1 unit of enzyme per µg of DNA. 50 µl was withdrawn from the first tube and transferred to the second tube to achieve 0.5 units of BclI/µg, and so on, each succeeding tube receiving half of the previous amount of BclI. The tubes were incubated at 37° C. for one hour, then heat-treated at 72° C. for 15 minutes and 15 µl from each was analyzed by agarose gel electrophoresis. Tubes exhibiting moderate, but incomplete digestion were chosen as the source of partial digest fragments for cloning and the completely digested DNA was combined separately. (The partial digestion tubes were the 0.25 u/µg, 0.12 u/µg, 0.06 u/µg and 0.03 u/µg tubes, while the 1.0 u/µg and 0.5 u/µg were the complete digestion tubes. The solutions were mixed together and used as described in step 4 below).

3. Construction of pEV328-8-6:pBR328 DNA (ATCC 37517) was partially digested with SspI endonuclease (New England Biolabs, Beverly, Mass.) by preparing 100 µl of 80 µg/ml pBR328, cesium-purification DNA in SspI buffer (100 mM NaCl, 10 mM Tris-HCl pH7.5, 10 mM MgCl$_2$, and 10 mM Beta-mercaptoethanol). Six units of SspI endonuclease were added and the mixture was placed immediately at 37° C. 15 µl aliquots were removed after 1.5, 2.5, 3.5, 4.5, 5.5, and 6.5 minutes at 37° C. SspI digestions were immediately terminated by heating at 72° C. for 15 minutes. 10 µl from each portion was analyzed by agarose gel electrophoresis. The 4.5- and 5.5 minute samples exhibited the greatest amount of linearized DNA and the smallest amount of uncut, supercoiled DNA. These tubes were selected for the next step, insertion of an SfiI linker into pBR328. 0.6 µg of SspI-partially digested pBR328 DNA (5 µl from the 4.5 minute tube, and 2.5 µl from the 5.5-minute tube), 9 µl distilled water, 2 µl 10X ligation buffer (see step 4 below), 1.5 µl 400 u/µl T4 DNA ligase (New England Biolabs, Beverly, Mass.), and 4 µl of 200 µg/ml SfiI unphosphorylated linker (GGCCGCAGCGGCC and GGCCGCTGCGGCC) (New England Biolabs, Beverly, Mass.) were mixed together and incubated overnight at room temperature. 5 µl were transformed into *E. coli* RRI cells and plated on chloramphenicol plates (see step 4 below). The DNA of 14 survivors was analyzed by the miniprep procedure (see step 9 below). Three survivors were found to contain the SfiI linker inserted into the first SspI site of pBR328, and were named pEV328-8.

To insert a second linker at the EcoRV site of pEV328-8, 50 µl of 80 µg/ml pEV328-8 in EcoRV buffer (150 mM NaCl, 6 mM Tris-HCl pH8.0, 6 mM MgCl$_2$ and 6 mM Beta-mercaptoethanol) containing 20 units of EcoRV endonuclease was incubated at 37° C. for two hours. 0.6 µg of the completely-digested DNA was ligated with 0.8 µg of the linker, as above. Six of the eight examined transformants were found to contain the linker at the EcoRV site of pEV328-8, and were named pEV328-8-6. A sample pEV328-8-6 has been deposited at the American Type Culture Collection on Feb. 8, 1990 and received ATCC accession No. 68217.

4. Ligation: The fragmented DNA from step 2 was ligated to pEV328-8-6 as follows: 6 µg of BclI-completely digested S. fimbriatus DNA (60 µl) and 6 µg of BclI-partially digested *S. fimbriatus* DNA (60 µl) were individually mixed with 3.0 µg of BamHI-cleaved and dephosphorylated pEV328-8-6 (7.5 µl). 20 µl of 10X ligation mix (500 mM Tris, pH 7.5, 100 mM MgCl$_2$, 100mM DTT, 5 mM ATP) was added, plus 110.5 µl of sterile distilled water to bring the final volume to 198 µl. 1.875 µl of concentrated T4 DNA ligase (2×10$^6$ u/ml) was added and the mixture was incubated at 16° C. for 4 hours then sterilized by the addition of 10 µl of chloroform. Approximately 125 µl of the ligated DNA was used to transform *E. coli* strain RR1 as follows: The DNA was mixed with 1.0 ml of SSC/CaCl$_2$ (50 mM NaCl, 5 mM sodium citrate, 67 mM CaCl$_2$) on ice and 2.0 ml of ice-cold competent *E. coli* RR1 (hsd R$^-$M$^-$, ATCC No. 31343) cells were added. After a 5-minute incubation at 42° C., the cells were diluted by the addition of 8 ml of Luria-broth (L-broth) then incubated at 37° C. for 1 hour.

5. Primary Cell Library: The transformed cell culture was briefly centrifuged, the supernatant discarded and the cells resuspended in 1.0 ml of L-broth. 200 µl portions were plated onto Luria-agar (L-agar) plates containing 100 µg/ml ampicillin. After overnight incubation at 37° C., the plates were each flooded with 2.5 ml of 10 mM Tris, pH 7.5, 10 mM MgCl$_2$ and the transformed colonies were scraped together and pooled to form the primary cell library.

6. Primary Plasmid Library: The primary plasmid library was prepared as follows: 2.5 ml of the primary cell library was inoculated into 500 ml of L-broth containing 100 µg/ml ampicillin. The culture was shaken overnight at 37° C. then centrifuged at 4000 rpm for 5 minutes. The supernatant was discarded and the cell pellet was resuspended in 10 ml of 25% sucrose, 50 mM Tris, pH 8.0, at room temperature. 5 ml of 0.25M EDTA, pH 8.0, was added, followed by 3 ml of 10 mg/ml lysozyme in 0.25M Tris, pH 8.0. The solution was left on ice for 3 hours, then 12 ml of lytic mix (1% Triton X-100, 50MM Tris, pH 8.0, 67 mM EDTA) was forcefully pipetted in, and the cell suspension gently swirled to achieve lysis. After lysis, the mixture was transferred to a 50 ml plastic centrifuge tube and centrifuged at 17000 rpm, 4° C. for 45 minutes. The supernatant was removed with a pipette. 20.0 gm of solid CsCl was weighed into a 50 ml plastic screw-cap tube and 22.0 gm of supernatant was pipetted into the tube and mixed. 1.0 ml of ethidium bromide solution (5 mg/ml ethidium bromide in 10 mM Tris, pH 8.0, 1 mM EDTA, 100 mM NaCl) was added to the mixture. The solution was transferred to two ⅝ in.×3 in. polyallomer centrifuge tubes and sealed. These tubes were then centrifuged in a Beckman Ti70 rotor for 42 hours at 44000 rpm, 17° C. To collect the plasmids, the tops of the tubes were pierced with a scalpel and the lower of the two fluorescent DNA bands was collected by syringe under ultraviolet light. The lower band from both tubes were combined into a screw-top glass tube and the ethidium bromide was removed by extracting four times with an equal volume of water-saturated ice-cold N-Butanol.

The extracted solution was transferred to dialysis tubing and dialyzed for 24 hours against 4 changes of DNA buffer. The dialyzed DNA solution was then transferred to a pre-weighed 50 ml sterile centrifuge tube and its volume was measured. 5M NaCl was added to a final concentration of 0.4M, then 2 volumes of isopropanol were added and mixed. The solution was stored overnight at −20° C. to precipitate the DNA. After precipitation, the solution was centrifuged at 15000 rpm, 0° C. for 15 minutes and the supernatant discarded. The tube was left on the bench to air-dry for 15 minutes, and then the DNA pellet was dissolved in 500 µl of DNA buffer and stored at −20° C. The DNA concentration of plasmids prepared in this way was found to be 100 to 200 µg/ml.

7. 108 µl (100 µg) of the plasmid library obtained in step 6 was electrophoresed for four hours in a 1% agarose gel containing 0.01% SDS. Using long-wave UV to view the gel, plasmids that migrated more slowly than the parent vector (eg. everything above the −2.8 kb marker, where pEV328-8-6 supercoiled plasmid runs) were cut from the gel and minced using a clean razor blade. The mixture was forced through a 22 gauge syringe into 5 ml 1x agarose gel buffer containing 0.01% SDS, and centrifuged at 17000 rpm for 45 minutes. The supernatant was precipitated with 0.5 ml 5M NaCl and 1.1 ml isopropanol at −20° C. overnight. The DNA was pelleted at 15000 rpm for 15 minutes. The pellet was resuspended in 500 µl 10 mM Tris pH8, 1 mM EDTA, phenol/chloroform extracted, chloroform extracted three times and precipitated again with 48 µl 15M NaCl and 1100 µl isopropanol at −20° C. for three hours. The pellet was rinsed with 70% isopropanol and air dried, and resuspended in a final volume of 100 µl 10 mM Tris pH8, 1 mM EDTA.

8. Digestion of Plasmid Pool: The gel-purified primary plasmid pool was digested to destroy non-SfiI methylase clones as follows: The plasmid DNA was diluted to 50 µg/ml in 10 mM Tris pH 8.0, 10 mM MgC12, 10 mM mercaptoethanol, 50 mM NaCl. A total of 120 µl was prepared. 8 u/µg SfiI was added and the mixture was incubated at 50° C. for 2 hours.

9. Transformation: A 12.5 µl sample from each tube was used to transform *E. coli* RR1. After the 3-minute heat step and 45 minutes of growth in Luria Broth at 37° C. the cell/DNA mixtures were plated onto L-agar plates containing 200 3 g/ml chloramphenicol. After overnight incubation at 37° C., the plates were examined. Digestion of the plasmid library with SfiI was found to have reduced the number of transformants by a factor of about $10^3$. Ten individual colonies were picked from the plates. Each colony was inoculated into 10 ml of L-broth containing chloramphenicol, to prepare a miniculture, and was also streaked onto L-agar plates containing chloramphenicol to prepare a master stock.

10. Analysis of surviving individuals: Ten of the surviving colonies obtained from section 9 were grown up in 10 ml cultures and the plasmids that they carried were prepared by the following miniprep purification procedure, adapted from the method of Birnboin and Doly (*Nucleic Acids Res.* 7:1513 (1979)).

Miniprep Procedure: Each culture was centrifuged. at 8000 rpm for 5 minutes; the supernatant was discarded and the cell pellet was resuspended in 1.0 ml of 25 mM Tris, 10 mM EDTA, 50 mM glucose, pH 8.0, containing 1 mg/ml lysozyme. After 10 minutes at room temperature, 2.0 ml of 0.2M NaOH, 1% SDS was added to each tube and the tubes were shaken to lyse the cells, then placed on ice. Once the solutions had cleared, 1.5 ml of 3M sodium acetate, pH 4.8, was added to each and shaken. The precipitates that formed were spun down at 15000 rpm, 4° C. for 10 minutes. Each supernatant was poured into a centrifuge tube containing 3 ml of isopropanol and mixed. After 10 minutes at room temperature, the tubes were spun again at 15000 rpm for 10 minutes to pellet the precipitated nucleic acids. The supernatants were discarded and the pellets were air-dried at room temperature for 30 minutes. Once dry, the pellets were resuspended in 850 µl of 10 mM Tris, 1 mM EDTA pH 8.0. 75 µl of 5M NaCl was added to each and the solutions were transferred to Eppendorf tubes containing 575 µl of isopropanol, and again precipitated for 10 minutes at room temperature. The tubes were then centrifuged for 45 seconds in a microfuge, the supernatants were discarded and the pellets were air-dried. The pellets were then dissolved in 500 µl of 10 mM Tris, 1 mM EDTA, pH 8.0, containing 100 µg/ml RNase and incubated for 1 hour at 37° C. to digest the RNA. The DNA was precipitated once more by the addition of 50 µl of 5M NaCl followed by 350 µl of isopropanol. After 10 minutes at room temperature, the DNA was centrifuged for 45 seconds, the supernatants were discarded and the pellets were redissolved in a final solution of 150 µl of 10 mM Tris 1 mM EDTA, pH 8.0. The plasmid minipreps were subsequently analyzed by digestion with SfiI.

Figure 2:
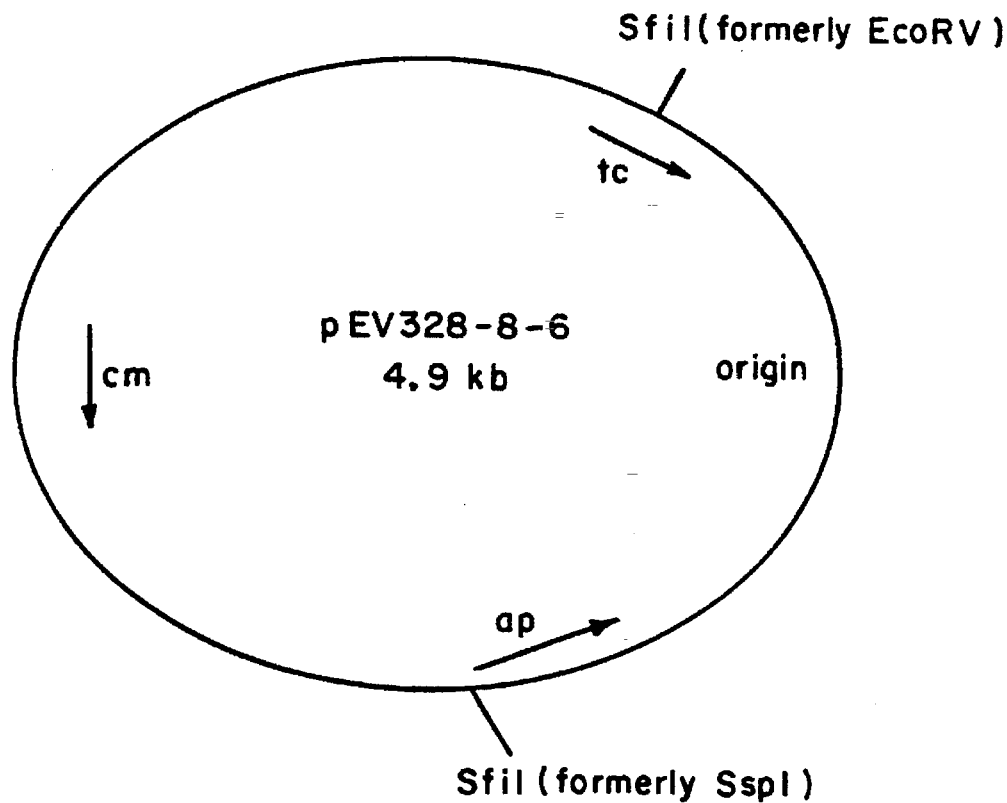
FIG. 2 is a map of the 4.9 kb cloning vector, pEV328-8-6.
Figure 5:
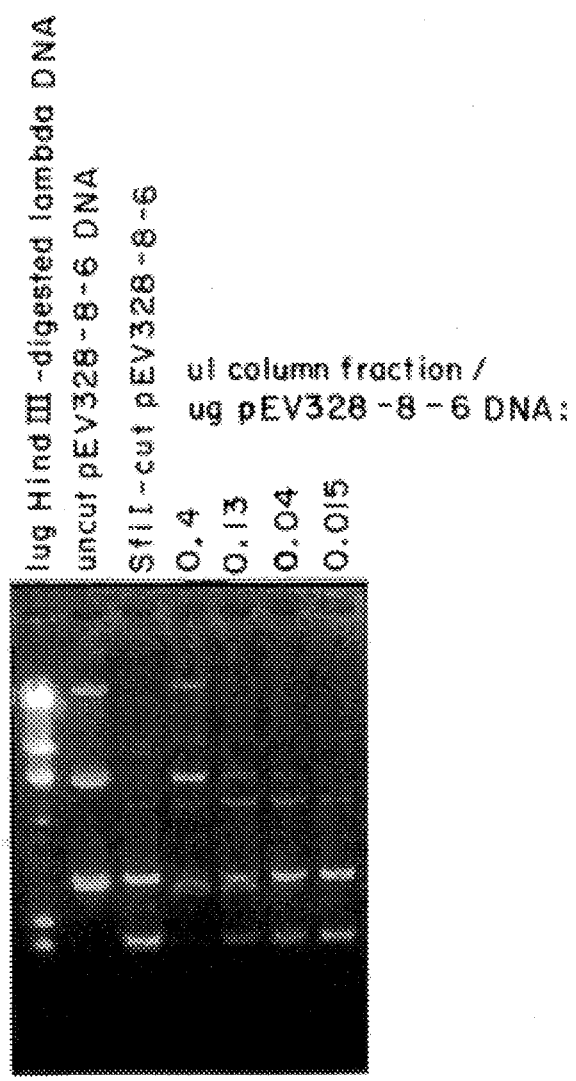
FIG. 5 is a photograph of an agarose gel illustrating SfiI modification methylase activity obtained from the cell extract of pEV123RM 612-16. 250 ul of 50 ug/ml pEV328-8-6 was prepared in 1x methylase buffer (50 mM Tris, pH7.5, 10 mM EDTA, 5 mM BME, 0.1 mM AdoMet). 50 ul was placed in each of 4 tubes. 25 ul was placed in each of two tubes, to be used as controls. 1 ul of column fraction was added to the first 50 ul tube and mixed. 25 ul was transferred to the 2nd 50 ul tube and mixed. 25 ul from the 2nd 50 ul tube was transferred to the 3rd 50 ul tube and mixed, and then 25 ul from the 3rd 50 ul tube was transferred to the 4th 50 ul tube and mixed. All tubes were incubated at 37° C. for one hour. 250 ul of the following mix was prepared: 50 mM Tris, pH8.0, 40 mM MgCl2, 5 mM BME, 200 units SfiI endonuclease. An equal volume of this mixture was added to each tube (except for the uncut pEV328-8-6 control tube) and incubated for one hour at 50° C. 25 ul from each tube was analyzed by gel electrophoresis.

11. Methylase Gene Clones (named pEV123RM612-16): Nine plasmids were found to be resistant to SfiI and to carry a 3.9kb BclI fragment (see FIG. 2). In each case the fragment was in the same orientation with respect to the plasmid's tetracycline-resistance-gene promoter. These nine plasmids were subsequently shown to carry the SfiI modification methylase gene. This was established by deleting the BclI insert and checking the remaining vector for intact, cleavable SfiI sites; and by an in vitro modification methylase assay performed on an extract prepared from *E. coli* into which the plasmid had been transferred by transformation, as follows:

A 500 ml culture of the clone to be tested was grown overnight in L-broth plus 100 µg/ml ampicillin at 37° C. and the cells were pelleted by centrifugation at 4000 rpm for 5 minutes. The supernatant was discarded and the pellet was resuspended in 7.5 ml of sonication buffer (20 mM $KPO_4$ pH7.4, 10 mM beta-mercaptoethanol). Once resuspended, the cells were sonicated for three 15-second bursts to disrupt the cells. The sonicated cells were centrifuged for 15 minutes at 10,000 rpm and the supernatant was used as the cell extract. The extract was purified on a 1 ml phosphocellulose column at 4° C. as follows: 0.4 ml 2M KCl was added to the extract to make the final concentration 0.1M KCl. The column was equilibrated with 3–4 ml 0.1M KCl, 20 mM KPO4 pH7.4, 10 mM Beta-mercaptoethanol and 5% glycerol. The extract was loaded onto the column, and the eluate was collected in 5-drop fractions. The column was washed with 3.5 ml of the above buffer, then 3.5 ml of the above buffer with the KCl concentration at 0.3M, then with the above buffer with the KCl concentration at 0.5M, and finally with the above buffer with the KCl concentration at 0.7M KCl. The conductivity of each 5-drop fraction was recorded to determine which fractions contained the initial increases in KCl concentration. Those tubes were assayed for methylase activity as follows: 1 µl column fraction was added to 50 µl of 50 µg/ml T4 DNA in methylase buffer (50 mM Tris, pH7.5, 10 mM EDTA, 5 mM beta-mercaptoethanol, 0.1 mM S-adenosyl methionine). After 1 hour at 37° C., 50 µl of the following mixture was added to each tube: 50 mM Tris, pH8.0, 40 mM MgC12, 5 mM beta-mercaptoethanol, 80 units/ml SfiI endonuclease, and 100 mM NaCl. The tubes, now containing 100 µl each, were incubated at 50° C. for 1 hour. A 25 µl sample from each tube was analyzed by gel electrophoresis. The tubes containing 0.3M and 0.5M KCl were found to contain the methylase activity at a titer of approximately 2500 units per ml, which corresponds to about 6000 units of SfiI methylase per gram of wet cell paste. (See FIG. 5)

12. The extract was also assayed for restriction endonuclease activity by incubating 1 µl of each column fraction with 35 µl of 50 mM Tris pH 8, 50 mM NaCl, 10 mM $MgCl_2$, 10 mM beta-mercaptoethanol, 50 µg/ml T4 DNA for 1 hour at 50° C. A 25 µl sample analyzed by electrophoresis showed no evidence of restriction endonuclease activity.

13. Location of the methylase gene within the 3.9 kb BclI insert: The SfiI methylase clone was digested with numerous restriction endonuclease to provide a restriction map of the cloned DNA. Using the map, various regions within the insert were deleted to determine the resulting effect on methylation. The location of the approximately 1 kb methylase gene within the 3.9 kb insert was then pinpointed, and the length of cloned DNA on either side of the gene was found to be approximately 0.6 and approximately 2 kb. The methylase clone did not contain enough DNA (0.6 kb) on the left side to encode a linked restriction endonuclease gene, and possibly did not contain enough DNA (approximately 2 kb) on the right of the methylase gene, since the distance between the two genes, the exact size of the genes, and whether or not they were linked was not known (see FIG. 3). The lack of SfiI endonuclease activity in the clone indicated that the restriction gene was either not present in the clones, or was present but not expressed. In the event that the restriction gene was present and not expressing, DNA and protein sequencing of the methylase clones was undertaken to determine whether part, all or none of the restriction gene was present in the clones as described in steps 19-21. In the event that the entire restriction gene was not present, the cloning of the larger regions of DNA adjacent to the methylase gene was achieved as described in steps 14-18.

14. A genomic map of the adjacent regions was determined by the Southern blot technique (Southern, E. 1975, *J. Mol. Bio.*, 98:503) using portion of the methylase clone as a probe, specifically, the approximately 1.7 kb BamHI-KpnI fragment which had been gel-purified and nick-translated with alpha $^{32}$P-ATP. Gel purification is described in step 7. The gel-purified probe was nick-translated as follows: 5 µl (0.5 µg) DNA, 1.5 µl buffer (500 mM Tris pH 7.5, 10 mM beta mercaptoethanol, 50 mM MgCl$_2$), 1 µl GTC (500 pmoles/µl), 5 µl alpha-$^{32}$P-dATP- (100 pmoles, 800 Curies/ millimole), 2 µl DNA polymerase I (20 units), and 1 µl DNAse I (1 µg/ml) were mixed together and incubated 16° C. for 2 hours. The mixture was then boiled for 10 minutes and placed immediately on ice.

The Southern blot was prepared as follows: *S. fimbriatus* DNA was digested separately with the restriction endonucleases AseI, BamHI, BclI, ClaI, DraI, EcoRI, EcoRV, NcoI, NdeI, NheI, NotI, PstI, PvuII, SalI, ScaI, SmaI, SpeI, SphI, and XhoI. The digests were electrophoresed on a 1.0% agarose gel. The gel was soaked in 0.25M HCl for 10 minutes; 0.4M NaOH, 0.8M NaCl for 30 minutes; and then in 0.5M Tris-HCl pH 7.5, 1.5M NaCl for 30 minutes. A nitrocellulose sheet was soaked briefly in water, then in 5 X SSC (0.75 M NaCl, 75 mM sodium citrate). The gel was placed on top of a ½ inch stack of chromatography paper (Whatman) in 300 ml 20 X SSC (3M NaCl, 0.3M sodium citrate), with the level of buffer just below the height of the stacked paper. The nitrocellulose sheet was placed on top of the gel and backed with chromatography paper (Whatman) to act as a wick. The sandwich was weighed down and transfer of the gel contents to the nitrocellulose sheet was allowed to proceed at room temperature overnight. The sheet was then rinsed in 1 X SSC for ten minutes and baked in a vacuum oven at 80° C. for 1.5 hours to fix the transferred DNA fragments to the nitrocellulose. The sheet was transferred to a plastic bag containing 15 ml of a solution composed of 3 ml of 10 g/l Ficoll, 10 g/l polyvinylpyrrolidone, 10 g/l bovine serum albumin; 4.5 ml of 20 X SSC; 1.5 ml 10% SDS; 3 ml 10% dextran sulfate; 3 ml water, and prehybridized by incubating at 65° C. with shaking for 3 hours. 7 µl radioactive probe was added to the bag, and incubation was continued at 65° C. shaking overnight. The nitrocellulose sheet was then washed three times for 5 minutes each at room temperature with 0.3M NaCl, 30 mM Sodium Citrate; and once for twenty minutes at 65° C. in the same buffer containing 0.5% SDS. The sheet was then air-dried and autoradiographed overnight.

Figure 4:
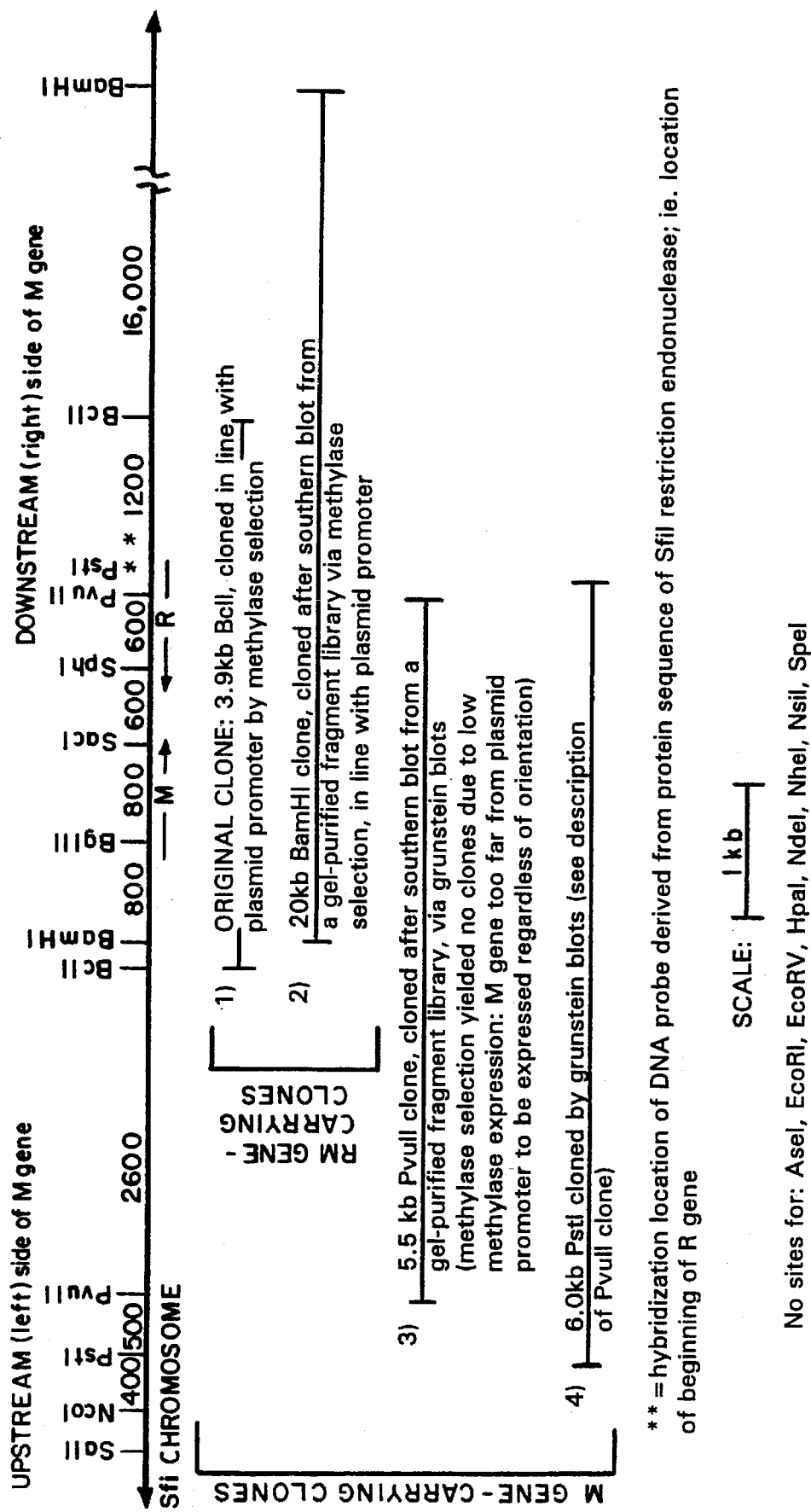
FIG. 4 is a restriction map of the entire approximately 23 kb of the *Streptomyces fimbriatus* DNA that has been cloned.

From the Southern blot data, the exact sizes of six methylase-encoding fragments were known. NcoI, PstI, PvuII, SalI fragments carry DNA to the left of the methylase gene; BamHI and SmaI carry DNA to the right (FIG. 4). The probe hybridized to a single 6-kb band in both the PstI-digest and the NcoI-digest, to an 8-kb band in the SalI-digest, a 5.5-kb band in the PvuII-digest, and a 20-kb band in both the BamHI and SmaI digests. The other bands were judged to be too large to clone.

15. Six libraries (BamHI, NcoI, PstI, PvuII, SalI, SmaI) were constructed and selected by the same procedures as steps 2-6 and 8-10 (step 7 was not done), with the following modification at steps 2 and 4: 30 µl (30 µg) SfiI chromosomal DNA was digested completely in 300 µl 10 mM Tris pH7.5, 10 mM MgCl$_2$, 150 mM NaCl, 10 mM mercaptoethanol containing excess BamHI (150 units) at 37° C. for 3 hours. The entire volume was electrophoresed in a 1% agarose gel containing 0.01% SDS for 5 hours. Using long wave UV to view the gel, the fragments within the size range of the known size of the methylase-gene-carrying fragment were cut out of the gel and minced with a clean razor blade. The fragments were purified following the same procedure as step 7. 15 µl (0.8 µg) was ligated to 2 µl (0.8 µg) of BamHI-cleaved and dephosphorylated pEV328-8-6 in 70 µl 1X ligation buffer containing 1200 units T4 DNA ligase at 16° C. for 4 hours. All 70 µl was transformed into RR1.

16. Identification of new BamHI methylase clones carrying a large region of DNA downstream from the methylase gene (designated pEV123RM603-2): 15 of the survivors from step 15 were from the BamHI library, and one of these was found to carry 20 kB BamHI fragment encoding the SfiI methylase gene. This clone overlapped the original BclI clone as indicated in FIG. 4, and carried a long enough length of DNA to encode a approximately 1 kb restriction endonuclease gene if it were linked downstream of the methylase gene. Methylase selection of the four libraries that were constructed to clone DNA upstream from the methylase were unsuccessful (PstI, PvuII, SalI, NcoI), leaving the upstream side of the methylase gene yet to be cloned (as described below, the cause was later shown to be lack of expression).

17. Obtaining new methylase clones carrying a large region of DNA upstream from the methylase gene (PstI clones were desingated pEV123RM604-19; PvuII clones were designated pEV123RM625-11): Since the new BamHI clone showed no endonuclease activity, attempts to clone upstream from the methylase gene were further pursued. The unsuccessful new libraries, as well as some older libraries, were probed with the methylase to see if the desired fragments had been cloned in the libraries or if they were absent. The results showed that the fragments were present in the libraries, suggesting that methylase selection was unsuccessful due to poor expression of the methylase clones. To isolate clones carrying the unexpressed methylase gene, Grunstein blots were used as described in the following step.

18. A protocol similar to that described in Maniatis, et al. was used to examine a total of approximately 3200 individual colonies from the PstI and PvuII libraries by Grunstein blots, again using the nick-translated BamHI-KpnI fragment as a probe (Maniatis, T., et al. *Molecular Cloning*, Cold Spring Harbor, 1982, p.313; Grunstein, M. and D. Hogness, 1975, *Proc. Natl. Acad. Sci.* 72: 3961) the disclosures of which are hereby incorporated by reference herein. The bacterial colonies were transferred to nitrocellulose filters by contact-lifts. The filters were immersed in 0.5M NaOH, 2M NaCl for 30 seconds; 0.5M Tris-HCl, pH 7.5, 3M NaCl for 1 minute; 0.3M NaCl, 0.03M sodium citrate, 0.1% SDS for 5 seconds; 0.3M NaCl, 0.03M sodium citrate for 10 seconds. The filters were air-dried, and then they were baked in a vacuum-oven at 80° C. for 30 minutes. The filters were prehybridized, and then hybridized with the 1.7 kb SfiI methylase gene probe, using the procedure described above. The filters were air-dried and autoradiographed overnight.

Clones carrying the methylase gene and DNA to the left as expected were isolated from both the PstI and PvuII libraries. These clones indeed expressed little or no methylase activity; the methylase gene was too far from any vector promoter. The overlap of these clones with the BamII and BclI clones is shown in FIG. 4.

19. With the recovery of the new clones, there was now enough DNA cloned on both sides of the methylase gene to encode a restriction endonuclease gene, if it were linked, regardless of which side encoded the linked gene. However, none of the clones expressed any restriction endonuclease activity. With still no proof that the two SfiI R-M genes were linked, SfiI restriction endonuclease was purified as close to homogeneity as possible for protein sequencing as follows:

One liter crude cell extract from 308 g *S. fimbriatus* was placed over a the following columns in the following order: heparin, DEAE-cellulose, affi-gel blue, monoQ HPLC and monoS HPLC resulting in ≧95% pure SfiI restriction endonuclease.

100 µl (2.5 µg) of the purified SfiI restriction endonuclease was used for amino terminal protein sequencing on Applied Biosystems Model 470A gas phase protein sequencer. The first 28 amino acid residues were sequenced as follows:

methionine - histidine - glutamine - aspartic acid - tyrosine - arginine - glutamic acid - leucine - undetermined - leucine - aspartic acid - glutamic acid - leucine - glutamic acid - undetermined - valine - glutamic acid - lysine - glutamine - threonine - leucine - arginine - undetermined - isoleucine - valine - glutamine - alanine - leucine.

20. Identification of restriction gene clones: Based on the above sequence, a 14-mer DNA oligo probe with 8-fold degeneracy was constructed:

ATGCA(T,C)CA(G,A)GA(C,T)TA

Only the first five amino acid residues were chosen for translation into DNA sequence because, although increasing DNA length increases hybridization specificity, in this case it also increases degeneracy and therefore reduces specificity. The original BclI clone, the subsequent BamHI clone carrying overlapping DNA downstream of the original clone, and the PstI clone carrying overlapping DNA upstream of the original clone, were digested with various restriction endonucleases and blotted onto nitrocellulose like the procedure described above (step 14). The DNA 14-mer was kinased in 26 µl as follows: 2.5 µl 10X kinase buffer (700 mM Tris-HCl pH7.6, 100 mM MgCl2, 50 mM DTT, 2.6 mM 5'-hydroxyl-terminated salmon sperm DNA), 5 µl 14-mer (1 O.D./ml), 12.5 µl dH20, 5 µl gamma32PATP (50 uCi), and 1 µl kinase (10 units), at room temperature for 1.3 hours. The entire volume was added to the pre-hybridized blot and shaken overnight at room temperature. The blot was washed and exposed as described in step 14. The results showed that the oligomer hybridized to a specific location on the BclI and BamHI clones but not to the PstI clone, allowing the exact location of the beginning of the SfiI restriction endonuclease gene to be pinpointed to within a particular 200 base pair region in the methylase clones (see FIG. 4). This is indirect but substantial proof that the SfiI R-M genes are linked and completely cloned together on the BamHI clone and at least partly on the BclI clone (step 21 showed that the BclI clone also contained the complete R-M genes).

21. DNA sequencing of the region confirmed the presence of the restriction gene, revealed its orientation, and provided data to use as a basis for subsequent manipulations of the recombinant plasmid to induce expression of the cloned restriction gene in *E. coli* as indicated in Example 2 below.

EXAMPLE 2

Overexpression of the SfiI Restriction Endonuclease Gene

Sequencing the DNA of the region and detailed mapping and deletion data maybe used in a number of approaches to obtain maximum expression of the cloned SfiI restriction endonuclease.

One such approach comprises inserting a promoter recognized strongly by *E. coli*, such as lambda pL, in direct proximity to the beginning of the SfiI restriction endonuclease gene. The strong promoter may be inserted into a suitable vector using known methods. One such suitable vector is pGW7 (ATCC 40166). Insertion of the strong promoter may be accomplished by identifying convenient restriction targets near both ends of the restriction gene and compatible restriction targets on the vector near the promoter, and transferring the restriction gene into the vector in such an orientation as to be under the translational control of the strong promoter.

SfiI endonuclease subclones containing a lambda pL promoter 0.5 kb from the start of the restriction gene did not exhibit amplified expression of the endonuclease as predicted. Therefore, in order to overexpress the cloned SfiI in accordance with the present invention, constructing this embodiment the restriction gene should be manipulated so that it is less than 0.5 kb downstream of the lambda pL promoter.

The level of expression of the restriction endonuclease gene may be determined using known methods, as described in steps 11–12.

SfiI may also be overexpressed by utilizing a strong ribosome binding site placed upstream of the SfiI restriction endonuclease gene to increase expression of the gene. See, Shine & Dalgarno, (1974) *Proc. Natl. Acad. Sci. USA* 71, 1342–1346.

A third approach for increasing expression of the SfiI restriction endonuclease gene comprises altering the DNA sequence of the gene by site-directed mutagenesis or resynthesis to contain initiation codons that are more efficiently utilized in *E. coli*.

A further approach for increasing expression of the SfiI restriction endonuclease gene comprises designing oligonucleotide primers for hybridization to both sides of the SfiI restriction endonuclease gene based on DNA sequence, to take advantage of the DNA polymerase chain reaction to amplify the restriction gene. The amplified fragment is inserted into an expression vector such as pGW7 (ATCC 40166) or pET3A (from William Studier, Brookhaven Nat. Lab., Upton, N.Y.). Both vectors contain a strong promoter and a ribosome binding site.

The SfiI modification methylase or endonuclease may be produced from clones carrying the SfiI modification gene and the overexpressed restriction gene by propagation in a fermenter in a rich medium containing appropriate antibiotics. The cells are thereafter harvested by centrifugation and disrupted by sonication to produce a crude cell extract containing SfiI methylase and restriction endonuclease activity.

The crude cell extract containing the SfiI methylase and endonuclease is purified by standard product purification techniques such as affinity-chromatography, or ion-exchange chromatography.

What is claimed is:

1. An isolated DNA fragment encoding an SfiI restriction endonuclease, said endonuclease having an N-terminal amino acid sequence comprising:

Met-His-Gln-Asp-Tyr-Arg-Glu-Leu-Xaa-Leu-Asp-Glu-Leu-Glu-Xaa-Val-Glu-Lys-Gin-Thr-Leu-Arg-Xaa-Ile-Val-Glu-Ala-Leu, wherein said isolated DNA fragment is obtainable from *Streptomyces fimbriatus* (ATCC 15051).

2. The isolated DNA of claim 1, further comprising an isolated DNA fragment encoding the SfiI methylase.

3. A DNA vector comprising the DNA fragment of claim 1 or 2.

4. A microbial host transformed by the vector of claim 3.

5. A method of producing SfiI restriction endonuclease comprising culturing a microbial host transformed with the vector of claim 3 under conditions suitable for expression of said endonuclease.

* * * * *

UNITED STATES PATENT AND TRADEMARK OFFICE
CERTIFICATE OF CORRECTION

PATENT NO. : 5,637,476
DATED : Jun. 10, 1997
INVENTOR(S) : Van Cott

It is certified that error appears in the above-identified patent and that said Letters Patent is hereby corrected as shown below:

Column 5, line 18, replace "unsuccesful" with --unsuccessful--

Column 6, line 28, replace "BamH1" with --BamHI--

Column 6, line 31, replace "HinP1" with --HinPI--

Column 13, line 20, replace "MgCl2" with --$MgCl_2$--

Column 14, line 33, replace "KPO4" with --$KPO_4$--

Column 14, line 48, replace "MgCl2" with --$MgCl_2$--

Column 17, line 54, replace "MgCl2" with --$MgCl_2$-- line 56, replace "dH20" with --$dH_2O$-- line 56, replace "gamma32PATP" with --gamma $^{32}P$ATP--

UNITED STATES PATENT AND TRADEMARK OFFICE
CERTIFICATE OF CORRECTION

PATENT NO. : 5,637,476
DATED : Jun. 10, 1997
INVENTOR(S) : Van Cott

It is certified that error appears in the above-identified patent and that said Letters Patent is hereby corrected as shown below:

Column 9, line 50, replace "1346)." with --1346). the disclosure of which is hereby incorporated by reference herein.--

Column 10, line 45, replace "1 mMEDTA" with --1 mM EDTA--

Column 11, line 2, replace "µl" with --21 µl--

Column 13, line 12, replace "15M" with --5M--

Column 17, line 24, replace "in ≥ 95%" with -- in ≥ 95% --.

Column 19, line 10, replace "GIn" with --Gln--

Column 19, line 11, replace "Gin" with --Gln--

Signed and Sealed this

Twenty-fourth Day of February, 1998

Attest:

BRUCE LEHMAN

*Attesting Officer*  *Commissioner of Patents and Trademarks*